(12) United States Patent
Thelen et al.

(10) Patent No.: US 11,478,395 B2
(45) Date of Patent: Oct. 25, 2022

(54) VESTIBULAR TRAINING APPARATUS AND METHOD OF USE

(71) Applicants: Sheila Thelen, Shafer, MN (US); Robert Briccotto, Middleton, DE (US); Jonathan Wampler, Newark, DE (US)

(72) Inventors: Sheila Thelen, Shafer, MN (US); Robert Briccotto, Middleton, DE (US); Jonathan Wampler, Newark, DE (US)

(*) Notice: Subject to any disclaimer, the term of this patent is extended or adjusted under 35 U.S.C. 154(b) by 351 days.

(21) Appl. No.: 15/929,295

(22) Filed: Apr. 23, 2020

(65) Prior Publication Data

US 2021/0330542 A1    Oct. 28, 2021

(51) Int. Cl.
*A61H 3/00* (2006.01)
*A61H 1/00* (2006.01)
*A61B 5/00* (2006.01)

(52) U.S. Cl.
CPC ........... *A61H 3/008* (2013.01); *A61B 5/4023* (2013.01); *A61H 1/005* (2013.01); *A61H 2003/007* (2013.01); *A61H 2201/1652* (2013.01); *A61H 2201/5053* (2013.01); *A61H 2203/0487* (2013.01)

(58) Field of Classification Search
CPC .. A61H 3/008; A61H 1/005; A61H 2003/007; A61H 2201/1652; A61H 2201/5053; A61H 2203/0487; A61H 2201/1215; A61H 2201/0161; A61B 5/4023
See application file for complete search history.

(56) References Cited

U.S. PATENT DOCUMENTS

| | | | | |
|---|---|---|---|---|
| 2,399,915 A | * | 5/1946 | Drake | A63B 22/025 482/7 |
| 3,408,067 A | * | 10/1968 | Armstrong | A63B 22/02 472/91 |
| 4,204,673 A | * | 5/1980 | Speer, Sr. | A63B 22/0292 601/40 |
| 4,410,175 A | * | 10/1983 | Shamp | A63B 69/0022 114/215 |
| 4,423,864 A | * | 1/1984 | Wiik | A63B 22/203 472/91 |
| 4,733,858 A | * | 3/1988 | Lan | A63B 21/4047 482/53 |
| 5,314,390 A | * | 5/1994 | Westing | A63B 21/4034 601/36 |

(Continued)

OTHER PUBLICATIONS

"Pro-Motion Advantage Off-Ice System"; http://www.pro-motionharness.com/redharness.html; Pro-Motion—The Ultimate in Training Technology; Canada West Skating International Ltd.; 2 pages.

(Continued)

*Primary Examiner* — Garrett K Atkinson

(57) ABSTRACT

A vestibular training apparatus and method as disclosed and claimed. Wherein the training apparatus comprises a motorized rotational platform, an adjustable body harness, a swivel coupling attached to the adjustable harness, a beam anchor, and pulley system. The pulley system in connection with the beam anchor allows a user to be lifted by the trainer after rotating on the motorized rotational platform, wherein the user continues to rotate after being lifted by the trainer as a result of inertia.

15 Claims, 8 Drawing Sheets

(56) References Cited

U.S. PATENT DOCUMENTS

| | | | | |
|---|---|---|---|---|
| 5,695,432 | A * | 12/1997 | Soderlund | A63B 21/4009 482/69 |
| 5,830,162 | A * | 11/1998 | Giovannetti | A61B 5/1038 482/69 |
| 6,135,928 | A * | 10/2000 | Butterfield | G06F 3/011 482/69 |
| 6,273,844 | B1 * | 8/2001 | Kelsey | A63B 21/00181 482/69 |
| 6,880,487 | B2 * | 4/2005 | Reinkensmeyer | A01K 15/027 119/728 |
| 7,125,388 | B1 * | 10/2006 | Reinkensmeyer | A63B 69/0064 601/5 |
| 7,255,666 | B2 * | 8/2007 | Cardenas | A63B 7/02 482/69 |
| 7,381,163 | B2 * | 6/2008 | Gordon | A63B 22/02 482/69 |
| 7,621,850 | B2 * | 11/2009 | Piaget | A63B 21/154 482/54 |
| 7,780,573 | B1 * | 8/2010 | Carmein | A63B 71/0622 482/4 |
| 8,002,674 | B2 * | 8/2011 | Piaget | A63B 23/0429 482/52 |
| 8,550,962 | B2 * | 10/2013 | Piaget | A63B 22/04 482/52 |
| 9,808,668 | B2 * | 11/2017 | Bucher | A61H 1/0262 |
| 10,232,209 | B2 * | 3/2019 | Pouchet | A63B 71/0622 |
| 10,272,284 | B2 * | 4/2019 | Bellman | A61H 3/008 |
| 10,478,371 | B2 * | 11/2019 | Stockmaster | G16H 40/63 |
| 10,492,977 | B2 * | 12/2019 | Kapure | A63B 23/04 |
| 10,561,885 | B1 * | 2/2020 | Lewis, Jr. | A63B 21/0603 |
| 10,967,220 | B2 * | 4/2021 | Gouzenko | A63G 23/00 |
| 11,083,933 | B1 * | 8/2021 | Wilder | A63B 21/4035 |
| 2012/0042917 | A1 * | 2/2012 | Workman | A61H 3/04 135/66 |
| 2014/0121063 | A1 * | 5/2014 | Wireman | A63B 71/023 482/23 |
| 2016/0038370 | A1 * | 2/2016 | Dreske | A61H 3/04 482/68 |
| 2016/0136477 | A1 * | 5/2016 | Bucher | A63B 69/0064 482/4 |
| 2016/0256346 | A1 * | 9/2016 | Stockmaster | G16H 40/63 |
| 2016/0256725 | A1 * | 9/2016 | Verdi | A63B 21/153 |
| 2017/0027803 | A1 * | 2/2017 | Agrawal | A61B 5/1122 |
| 2017/0232289 | A1 * | 8/2017 | Pouchet | A63B 23/03533 482/93 |
| 2018/0140496 | A1 * | 5/2018 | San | A61H 1/02 |
| 2018/0214336 | A1 * | 8/2018 | Bellman | A63B 22/0046 |
| 2019/0183715 | A1 * | 6/2019 | Kapure | G16H 50/20 |
| 2019/0184227 | A1 * | 6/2019 | Gouzenko | G06F 1/1694 |
| 2019/0307982 | A1 * | 10/2019 | Brodsky | A61M 21/00 |
| 2019/0366141 | A1 * | 12/2019 | Cylvick | A63B 21/4011 |
| 2021/0137768 | A1 * | 5/2021 | Buswell | A61G 7/1007 |
| 2021/0220700 | A1 * | 7/2021 | Wilder | A63B 1/00 |
| 2021/0229819 | A1 * | 7/2021 | Lemke | H02G 1/02 |
| 2021/0275843 | A1 * | 9/2021 | Lucas | A61H 3/008 |
| 2021/0401659 | A1 * | 12/2021 | Ookoba | A61H 3/00 |
| 2022/0142290 | A1 * | 5/2022 | Pesce | A43B 3/34 |
| 2022/0152452 | A1 * | 5/2022 | Fung | A63F 13/40 710/1 |

OTHER PUBLICATIONS

"Spinner with Motor"; https://www.bronsonfigureskating.com; Bronson Spinners—Elite Figure Skaters Spinner Training System; 6 pages.

* cited by examiner

VESTIBULAR TRAINING APPARATUS AND METHOD OF USE

TECHNICAL FIELD

The present disclosure relates to a vestibular training apparatus and method of use. Vestibular training is beneficial to increase coordination, balance, dual hemispheric brain function, and cognition in users. In addition, vestibular training is as helpful to autism, mild traumatic brain injury (mTBI), traumatic brain injury (TBI), and post-concussion therapy.

BACKGROUND

Devices designed to enhance dual hemispheric left and right brain connectivity are beneficial in general to cognitive health. Left and right brain connectivity are enhanced by many therapeutic and brain training techniques, one of which is vestibular training.

In particular, individuals with autism, mTBI, TBI and concussions have been shown to benefit from vestibular training and therapy. The method implements a type of rotational motion where limbs cross the medial axis. In addition, individuals that perform fast rotation sports which require a high degree of balance and coordination, such as figure skating, may also benefit from vestibular training exercises.

Development of the central nervous system, specifically vestibular training is beneficial to cognition, perceptual motor, and sensory motor skills. Specifically, vestibular training is beneficial to the development of skills such as auditory learning, visual perception, attention, and focus. In addition, vestibular training benefits, hand-eye coordination, ocular motor control, and postural adjustment. Vestibular training also benefits tactile and proprioception parts of the central nervous system.

The object of the invention is a vestibular training apparatus and method utilized for enhancement of cognitive function. Such an apparatus and method may be utilized by an individual with a disorder such as autism, mTBI, TBI, post-concussion, or any individual seeking to enhance their cognitive function.

SUMMARY

The present disclosure describes a vestibular training method and apparatus. The apparatus and method both comprise a motorized rotational platform [8], an adjustable body harness [1] worn by a user [3], spreader bar assembly [11] disposed above the user, a swivel coupling [2] connectively attached to the harness, [1], a beam anchor [4], and a pulley system [5] attached to the beam anchor [4] and harness [1], such that the user [3] may be lifted by a trainer [6] from the motorized rotational platform [8].

In use the body harness [1] is adjusted to the size of the user [3] by means of a variable length waist band and variable length shoulder straps.

In use, a motorized rotational platform [8] will rotate a user [3] at variable speeds. The user [3] is disposed in an adjustable body harness [1], said harness connectively attached to a swivel coupling [2] via a pulley system [5]. Said pulley system also attached to a beam anchor [4]. A trainer [6] may then lift the user [3] up from the rotational platform [8], allowing the user [3] to rotate about the swivel coupling [2] along the vertical axis [14]. The trainer [6] may then gently lower the user [3] back on the rotational platform [8].

Via the use of a pulley system [5], a trainer [6] may easily lift a user [3], even where a user [3] is much larger than the trainer [6]. In one embodiment, the trainer [6] may utilize a mechanical system to manipulate the pulley system [5] and lift the user [3].

DETAILED DESCRIPTION

The present disclosure describes a vestibular training apparatus and method of use.

An apparatus is disclosed. Said apparatus comprises a motorized rotational platform [8], an adjustable harness [1], spreader bar assembly [11], swivel coupling [2], pulley system [5] and beam anchor [4].

In one embodiment, said swivel coupling [2] is attached to the harness [1] by means of a high tensile strength industrial rope [10]. In one embodiment, the adjustable harness [1] is constructed of nylon webbing material. In one embodiment, said adjustable harness [1] may be secured about the ribs of the user [3].

Figure 1:
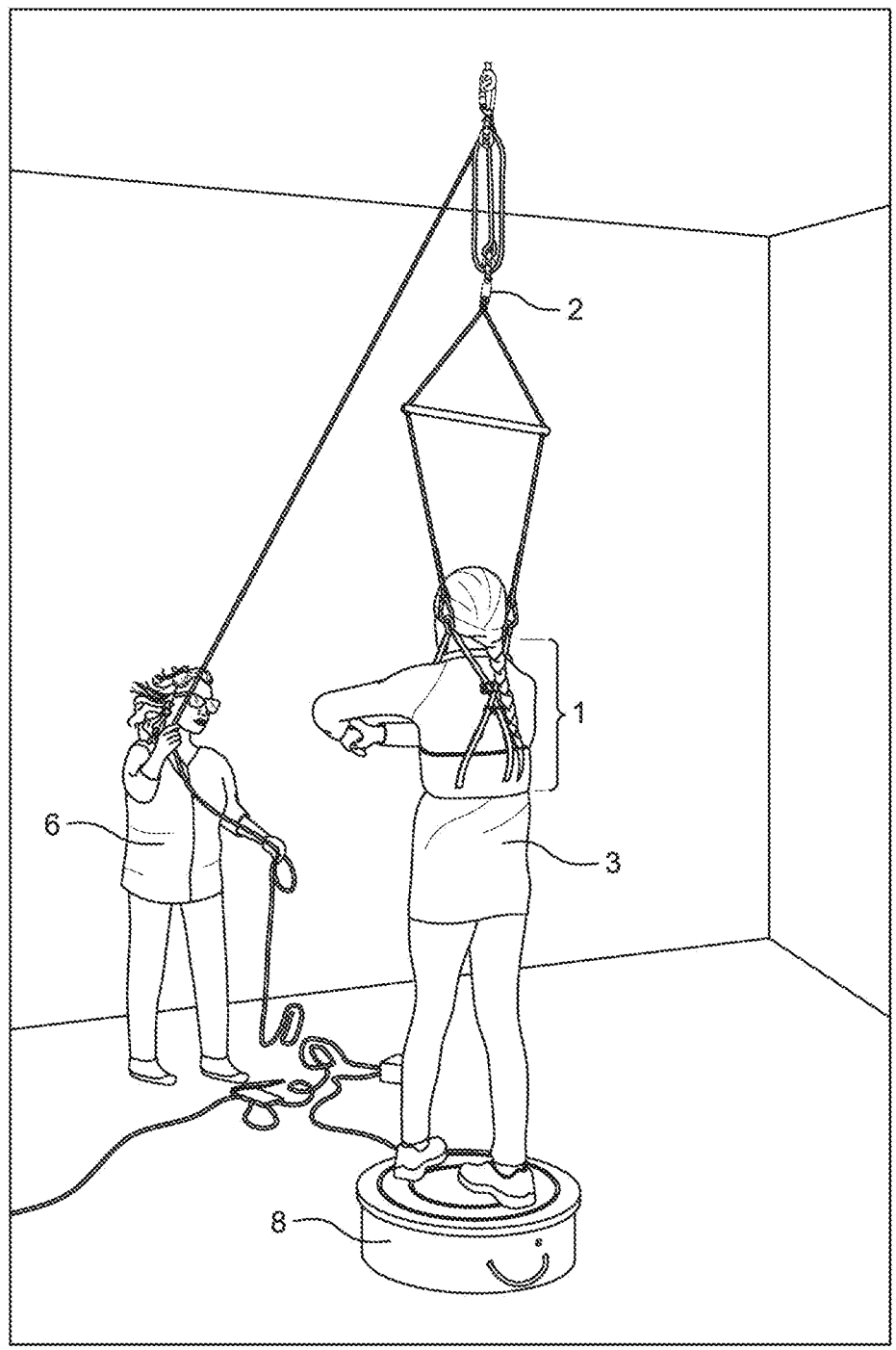
FIG. 1 is a slightly elevated perspective view of a vestibular training apparatus with a user disposed therein and trainer manipulating the device.
Figure 2:
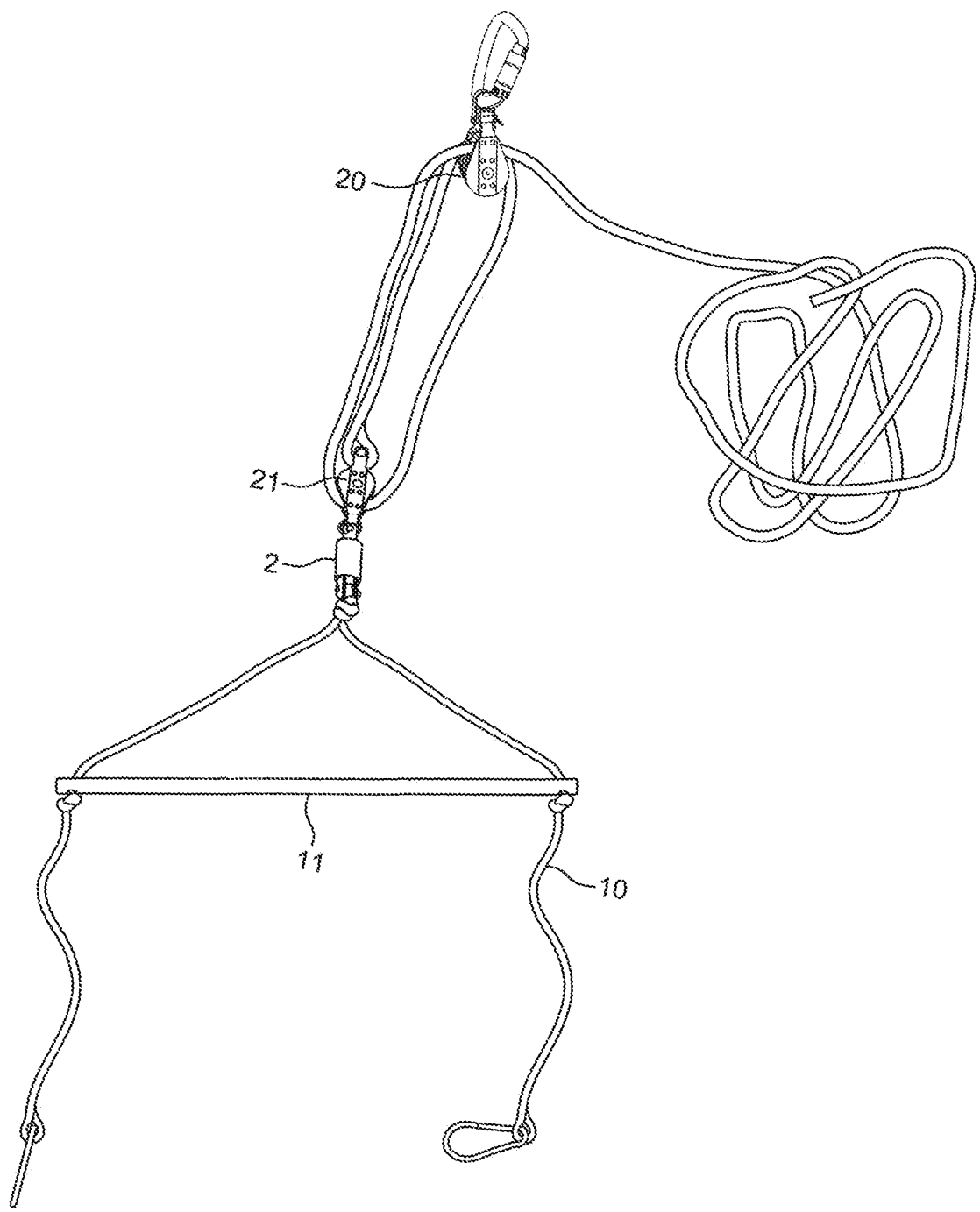
FIG. 2 is a perspective view the spreader bar assembly, swivel coupling, pulley system with upper and lower elements, and carabineer attachment without a user.
Figure 3:
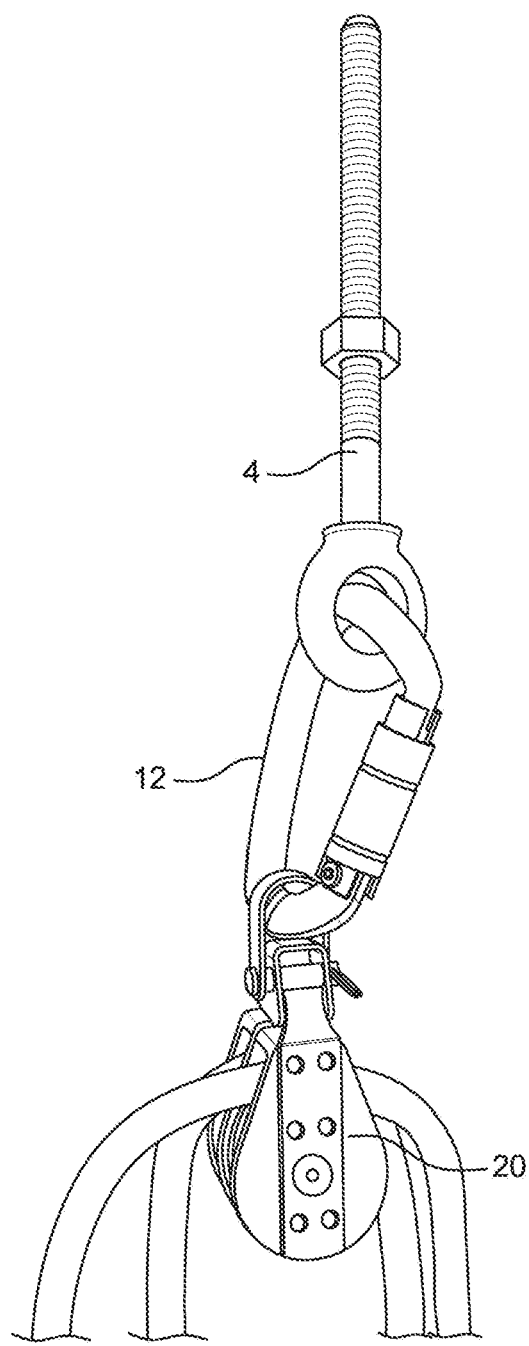
FIG. 3 is a perspective view of the beam anchor, carabineer, and upper element of the pulley system.
Figure 4:
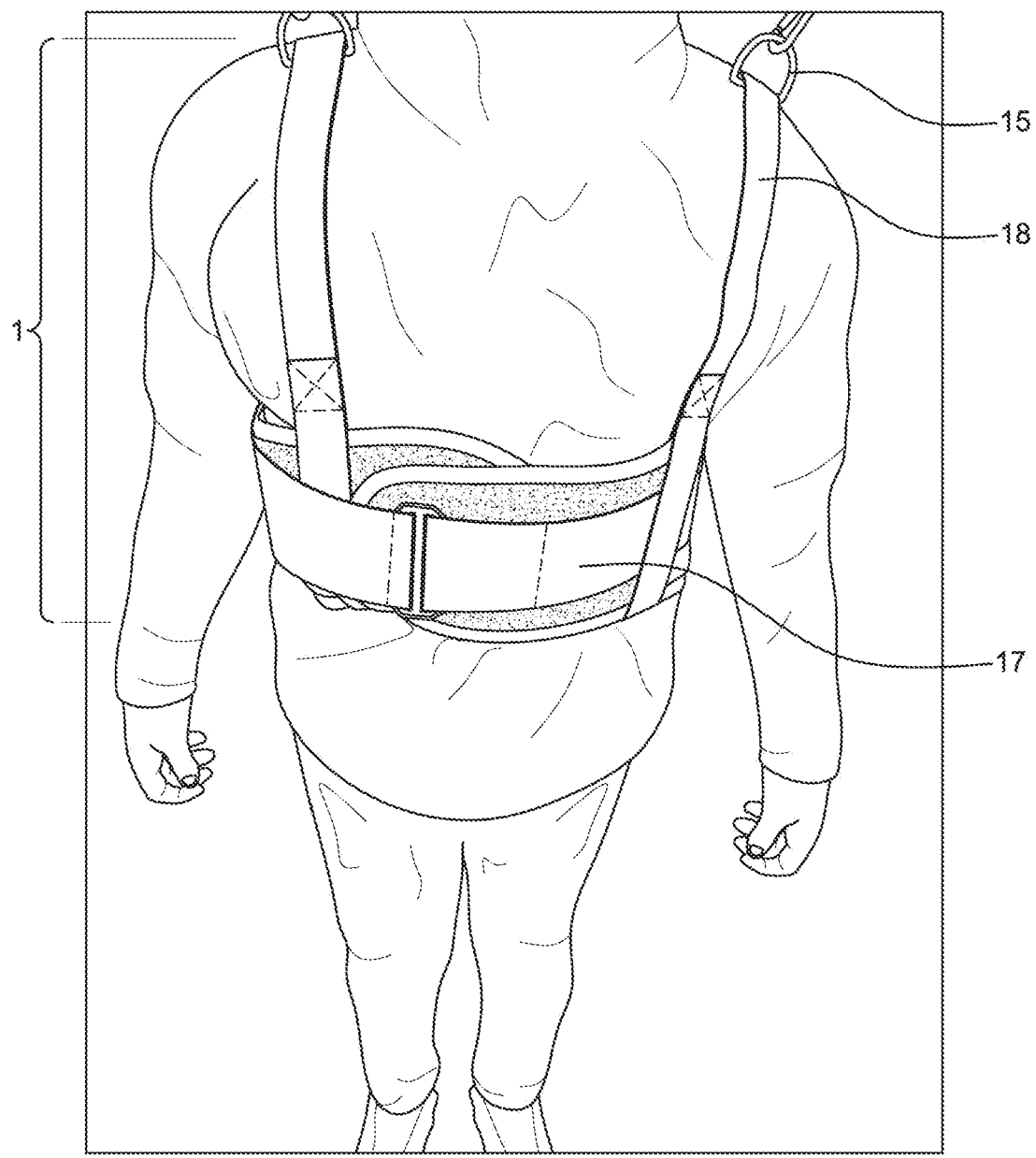
FIG. 4 is a perspective view of the front of the harness.
Figure 5:
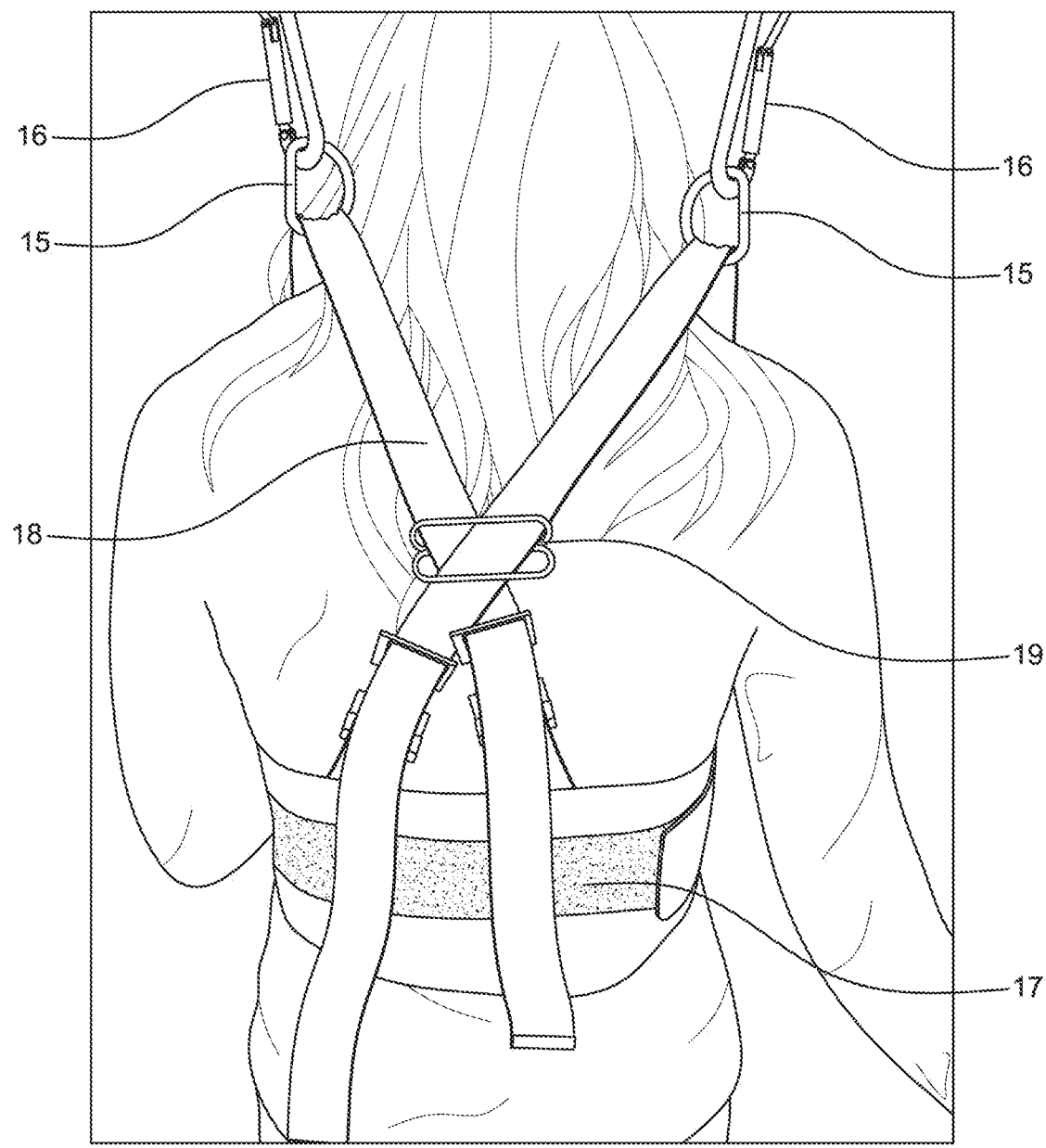
FIG. 5 is a perspective view from the back of the harness.
Figure 6:
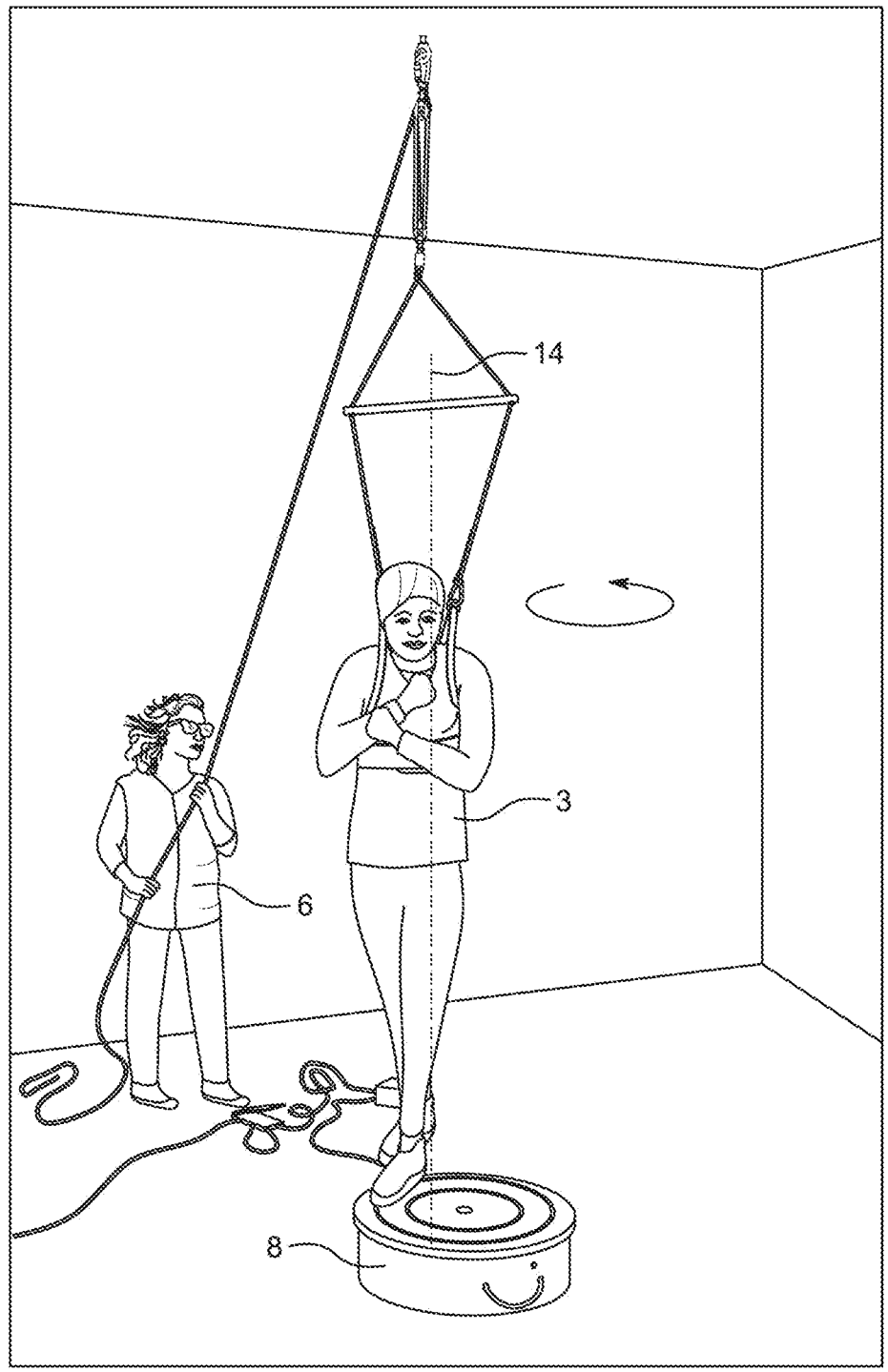
FIG. 6 is a perspective view of the apparatus with a user lifted from the rotational platform, and a trainer manipulating the pulley system.
Figure 7:
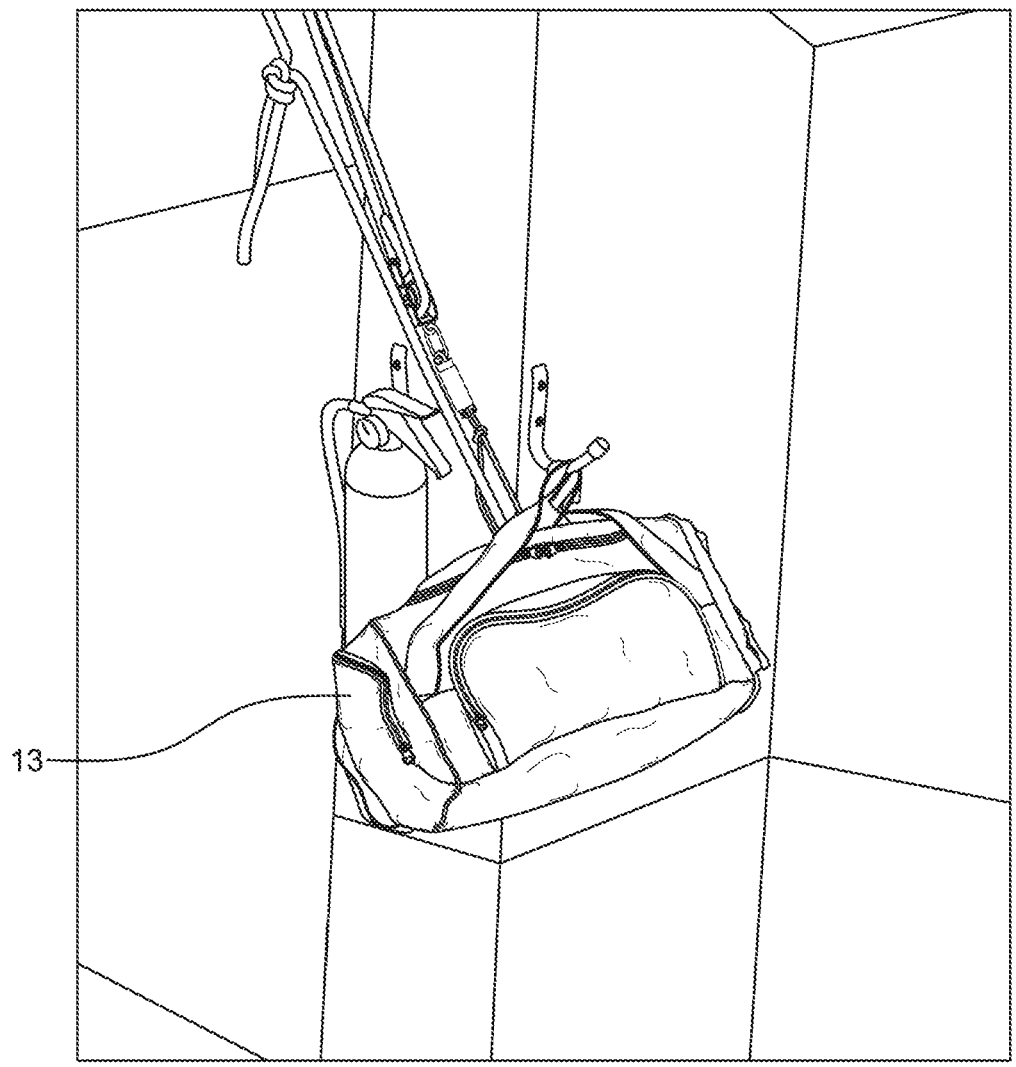
FIG. 7 is a perspective view of a storage bag.
Figure 8:
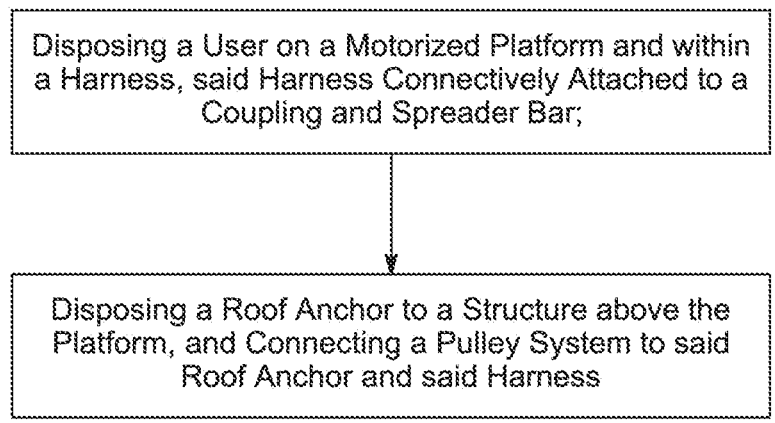
FIG. 8 is a flow diagram illustrating an example method.

Said swivel coupling [2] is configured such that one end of the swivel coupling [2] may rotate 360 degrees as orientated to the other end of the swivel coupling [2] along a vertical axis. Said axis of orientation is shown by dotted line [14] in FIG. 6. In one embodiment the upper end of the swivel coupling [2] is connected by means of a rope [10] or cable to the beam anchor [4], and the bottom portion of the swivel coupling [2] is coupled to the harness [1] by means described below.

In one embodiment, the swivel coupling [2] is configured such that minimal resistance is provided by the swivel coupling [2], thus a user [3] may rotate freely. The rotational velocity of the user [3] is dependent on the motorized rotational platform [1] or user [3] inertia.

A beam anchor [4] is disposed above the user [3]. In one embodiment, a pulley system [5] is connectively coupled to the beam anchor [4] and swivel coupling [2]. In one embodiment, a trainer [6] may manipulate the pulley system [5] to lift the user [3]. In another embodiment, a mechanical means is used to lift the user [3].

To use the apparatus and practice the method, the user [3] will stand on a motorized rotational platform [8]. Various commercial rotational platforms are available such as those offered by R&J Spinners. In one embodiment, the motorized rotational platform [1] will rotate, in a velocity set by a trainer [6] or user [3] to a variable scale ranging of one to one hundred. A higher velocity of rotation may be used where a user [3] has utilized the apparatus and method more often.

Said motorized rotational platform [8] must be of requisite size to accommodate the length of a foot for an adult or youth person. Also, the motorized rotational platform [8] must be of requisite power to rotate an adult or a youth ranging from 20 to 400 pounds.

In one embodiment, a user [3] will stand on the motorized rotational platform [8] for a period of one to several seconds and be rotated along with the rotational platform around a vertical axis. The user [3] may then jump and be suspended by the adjustable harness [3], swivel coupling [2], beam anchor [4], and pulley system [5].

In another embodiment, the trainer [6] may lift the user [3] from the motorized rotational platform [8] utilizing the harness [1], swivel coupling [2], beam anchor [4] and pulley system [5]. Such a lift can be made by the trainer [6] manually, or by mechanical means.

Once in the air, the user [3] will rotate about the swivel coupling's [2] vertical axis [14] for a period of one second or several seconds as a result of inertial rotation provided by the motorized rotational platform [8]. The amount of time spent rotating by the user [3] will vary depending on the training regime incorporated.

Various adjustable harness [1] embodiments may be utilized. In one embodiment, an adjustable harness [1] configured to fit snugly around the ribs of a user [3] will be utilized. Such a harness allows a user [3] a full range of motion in their legs and thus confers the ability to more closely control a rate of rotation.

In one embodiment, said harness [1] comprises nylon webbing material. In one embodiment, an adjustable harness [3], includes a waist belt [17] configured to adjust the harness. In one embodiment, said harness [1] also comprises shoulder straps [18], and load bearing D-rings [15].

In one embodiment, said harness [1] is adjustable by means of a metal loop [19] disposed on the back of the user [3]. Said nylon harness may be loosened or tightened by threading through a metal loop [19]. Said shoulder straps [18] are connectively coupled to the waist belt [17] of the harness [1], and connect to the apparatus is by means of the D-rings [15] disposed on the shoulder straps [18].

In one embodiment a spreader bar assembly [11] may be disposed between the adjustable harness [1] and the swivel coupling [2]. High tensile strength industrial cable or rope [10] is connectively attached to the D-rings [15] by means of a clip [16], each clip disposed on the two shoulder straps of the harness [1]. In one embodiment, a spreader bar [11] is disposed between the rope or cable at a point above the user's [3] head, at a point lower than the connection to the swivel coupling [2].

In this way, the high tensile strength industrial cable or rope [10] are less likely to interfere with the user [3] while rotating. The apparatus is more secure, and allows for greater rotational velocity, in the embodiment with a spreader bar assembly [11] as well.

Various embodiments of swivel coupling [2] are also disclosed. The swivel coupling [2] is capable of rotational 360 degrees about its vertical axis [14]. In one embodiment, said swivel coupling [2] comprises two ends, wherein each end may rotate 360 degrees in a vertical axis via a swivel mechanism as compared to the other end of the swivel coupling [2]. Said swivel coupling [2] is configured such that it will support the weight of an adult or youth, ranging from 20 to 400 pounds.

In another embodiment, said swivel coupling [2] utilizes other described joint configurations, such that the harness [1] secured to one end of the swivel coupling [2] may rotate 360 degrees along the vertical axis as compared to the other end of the swivel coupling [2] which is coupled to the beam anchor [4].

The beam anchor [4] must be of sufficient strength to support the weight of an adult or youth ranging from 20 to 400 pounds. Said beam anchor [4] is secured to a joist, truss, or other load bearing structure within a building or self-standing lift.

In one embodiment, the beam anchor [4] comprises an eye bolt. In another embodiment, the beam anchor [4] is of a different shape or material configured to be connectively coupled to a pulley system [5]. In one embodiment, a carabineer [12] is attached to said beam anchor [4] and the pulley system [5].

In one embodiment, said pulley system [5] comprises an upper [20] and lower [21] pulley element. Said beam anchor [4] is connectively coupled to an upper [20] pulley element, and the lower pulley element [21] is connectively coupled to the swivel coupling [2]. Said, pulley tackle systems are of a type conventionally utilized.

Also disclosed is a storage bag [13]. Said bag is configured to store any of the harness [1], pulley system [5], spreader bar assembly [11] or rope or cable used by the apparatus secure, and undamaged.

The invention claimed is:

1. A vestibular training apparatus for a user; the vestibular training apparatus comprising:
   a body harness configured to receive the user;
   a swivel coupling connectively coupled to the harness;
   a spreader bar disposed below the swivel coupling;
   a beam anchor
   a pulley system connectively coupled to the beam anchor and the harness; and
   a motorized platform disposed beneath the pulley system, wherein the motorized platform can rotate the user.

2. The vestibular training apparatus of claim 1, wherein the swivel coupling is configured to rotate 360 degrees oriented around the beam anchor.

3. The vestibular training apparatus of claim 1, wherein the beam anchor is connectively coupled to a structure utilizing an eye bolt.

4. The vestibular training apparatus of claim 1, wherein the beam anchor is connectively coupled to a carabineer, said carabineer connectively coupled to the pulley system.

5. The vestibular training apparatus of claim 1, wherein the pulley system comprises an upper pulley element, and lower pulley element.

6. The vestibular training apparatus of claim 5, wherein the pulley system includes a rope, said rope configured to be manipulated by a trainer.

7. The vestibular training apparatus of claim 5, wherein the pulley system is manipulated by mechanical manipulation.

8. The vestibular training apparatus of claim 1, wherein at least one of the body harness, swivel coupling, spreader bar, beam anchor, pulley system, and motorized platform is secured in a storage bag.

9. A method of conducting vestibular training comprising;
   disposing a user on a motorized platform and within a harness, said harness connectively coupled to a swivel coupling and spreader bar;
   disposing a beam anchor to a structure above the platform, and connecting a pulley system to said beam anchor and said harness, wherein the motorized platform is disposed beneath the pulley system; and further comprising rotating the motorized platform to rotate the user.

10. A method of claim 9, wherein the motorized platform includes a variety of settings such that the speed of rotation may be varied.

11. A method of claim 9, wherein the user is lifted via the pulley system and beam anchor.

12. A method of claim 9, wherein the user rotates relative to the beam anchor.

13. A method of claim 9, wherein a motorized means is utilized to manipulate the pulley system.

14. A method of claim 9, wherein a user undergoes a plurality of lifting events.

15. A method of claim 9, wherein the harness is secured to the user's ribs.

* * * * *